United States Patent
Reymond et al.

(10) Patent No.: US 6,482,607 B1
(45) Date of Patent: *Nov. 19, 2002

(54) EXPRESSION VECTOR FOR USE IN A ONE-STEP PURIFICATION PROTOCOL

(75) Inventors: Christophe Dominique Reymond, Prilly (CH); Nicolas Joseph Fasel, Epalines (CH)

(73) Assignee: RMF Dictagene S.A., Prilly (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/332,902

(22) Filed: Jun. 15, 1999

(30) Foreign Application Priority Data

Jun. 16, 1998 (EP) .............................. 98202018

(51) Int. Cl.⁷ ........................ C12N 15/63; C12N 15/12; C07K 14/47
(52) U.S. Cl. .................. 435/69.1; 435/69.7; 435/288.6; 435/320.1; 536/23.4; 536/23.5; 530/350
(58) Field of Search ............................... 435/69.1, 69.7, 435/257.3, 320.1, 288.6; 530/350; 536/23.4, 23.5

(56) References Cited

U.S. PATENT DOCUMENTS 5,677,144 A * 10/1997 Ullrich et al. ............. 435/69.1

FOREIGN PATENT DOCUMENTS

WO 92/20806 11/1992

OTHER PUBLICATIONS

Taylor, et al., "Carbohydrate–recognition Domains as Tools for Rapid Purification of Recombinant Eukaryotic Proteins", Biochemical Journal, vol. 274, 1991, pp. 575–580, XP002120284, ISSN: 0264–6021.

Marion M. Bradford, "A Rapid And Sensitive Method For The Quantitation Of Microgram Quantities Of Protein Utilizing The Principle Of Protein–Dye Binding," Analytical Biochemistry 72, 1976, pp. 249–255.

Jin–Soo Kim Ronald T. Raines, "Ribonuclease S–peptide as a Carrier in Fusion Proteins," Protein Science, 1993, pp. 348–357.

Z. Wilczynska and P. R. Fisher, "Analysis of a Complex Plasmid Insertion in a Phototaxis–Deficient Transformant of *Dictyostelium discoideum* Selected on a *Micrococcus luteus* Lawn," Plasmid 32, 1994, pp. 182–195.

Anjard et al., "Overexpression of Dd PK2 Protein Kinase Causes Rapid Development and Affects the Intracellular cAMP Pathway of *Dictyostelium Discoideum*," Development 115, 1992, pp. 785–790.

Barondes et al., "Discoidin I and Discoidin II Are Localized Differently in Developing *Dictyostelium Discoideum*," The Journal of Cell Biology, vol. 96, Jan. 1983, pp. 291–296.

Barondes et al., "Discoidin I, an Endogenous Lectin, Is Externalized from *Dictyostelium Discoideum* in Multilamellar Bodies," The Journal of Cell Biology, vol. 100, Jun. 1985, pp. 1825–1833.

Boulanger et al., "Formation of the Circumsprozoite Protein of *Plasmodium Falciparum* in *Anopheles Stephensi*," Acta Tropica 45, 1988, pp. 55–65.

Caspers et al., "The Circumsporozoite Protein Gene From NF54, a *Plasmodium Falciparum* Isolate Used in Malaria Vaccine Trials," Molecular and Biochemical Parasitology 35, 1989, pp. 185–189.

Choi et al., "A Modified Coomassie Blue Staining of Proteins in Polyacrylamide Gels with Bismark Brown R," Analytical Biochemistry 236, 1996, pp. 82–84.

Cooper et al., "Discoidin–Binding Polysaccharide from *Dictyostelium Discoideum*," The Journal of Biological Chemistry, vol. 258, No. 14, Issue of Jul. 25, 1983, pp. 8745–8750.

Vidal F. de la Cruz et al., "Variation Among Circumsporozoite Protein Genes from Rodent Malarias," Molecular and Biochemical Parasitology, 28, 1988, pp. 31–38.

Emslie et al., "From Virusto Vaccine: Developments Using the Simple Eukaryote, *Dictyostelium Discoideum*," Trends in Microbiology, Opinion, vol. 3, No. 12, Dec. 1995, pp. 476–479.

Frazier et al., "Purification and Comparisonof Two Developmentally Regualted Lectins from *Dicyostelium Discoideum* Discoidin I and II," The Journal of Biological Chemistry, vol. 250, No. 19, issue of October 10, pp. 7714–7721.

KunLiang Guan and Jack E. Dixon, "Eukaryotic Proteins Expressed in *Escherichia Coli*: An Improved Thrombin Cleavage and Purification Procedure of Fusion Proteins with Glutathione S–Transferase," Analytical Biochemistry 192, 1991, pp. 262–267.

(List continued on next page.)

Primary Examiner—John S. Brusca
(74) Attorney, Agent, or Firm—Pillsbury Winthrop LLP

(57) ABSTRACT

High expression levels and simple downstream processing are essential for the production of recombinant proteins at low cost. We report here a new expression vector which allows production of fusion proteins in *Dictyostelium discoideum*. We made use of the ability of Discoidin I to bind Sepharose-4B to set up a nearly single step purification procedure. The Discoidin I coding region was fused to several forms of the malaria parasite CSP gene in a Dictyostelium expression vector, allowing intracellular accumulation as well as partial secretion via a pathway unrelated to the endoplasmic reticulum and Golgi. The fusion proteins present in cell extracts were affinity-purified over Sepharose-4B columns. Addition of a signal peptide allowed endoplasmic reticulum targeting and glycosylation of the fusion protein. Inclusion of a thrombin cleavage site allowed to cleave Discoidin from the CSP protein. The use of stable and low cost Sepharose 4B as affinity matrix should allow large-scale preparations.

16 Claims, 6 Drawing Sheets

OTHER PUBLICATIONS

Figure 1:
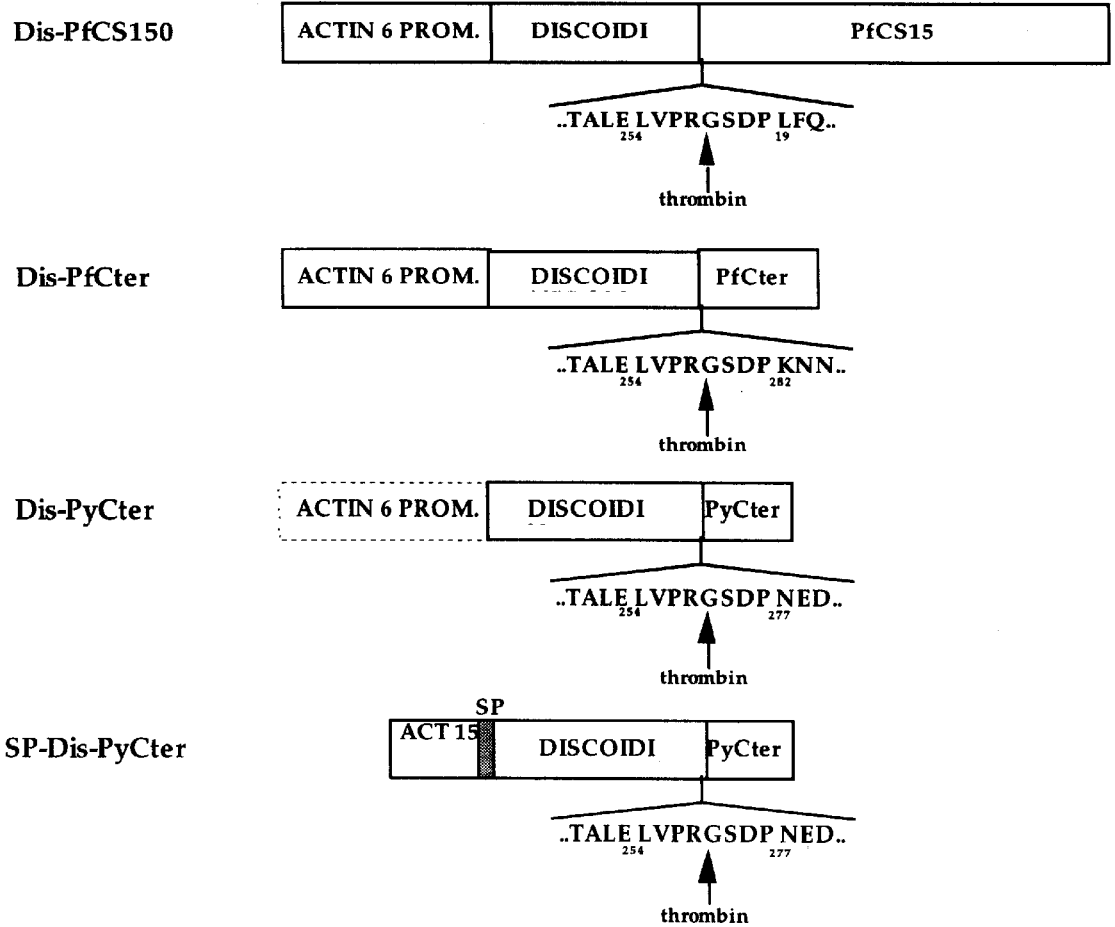

Guan et al., "Cloning and Expression of a Protein–Tyrosine–Phosphatase," Proc. Natl. Acad. Sci. USA, vol. 87, Feb. 1990, pp. 1501–1505.

Knecht et al., "Developmental Regulation of *Dictyostelium Discoideum* Actin Gene Fusions Carried on Low–Copy and High–Copy Transformation Vectors," Molecular and Cellular Biology, Nov. 1986, pp. 3973–3983.

Kroll et al., "A Multifunctional Prokaryotic Protein Expression System: Overproduction, Affinity Purification, and Selective Detection," DNA and Cell Biology, vol. 12, No. 5, 1993, pp. 441–453.

U. K. Laemmli, "Cleavage of Structural Proteins During the Assembly of the Head of Bacteriophage T4," Nature, vol. 227, Aug. 15, 1970, pp. 680–685.

Lavallie et al., "A Thioredoxin Gene Fusion Expression System That Circumvents Inclusion Body Formation in the *E. Coli* Cytoplasm," BIO/Technology, vol. 11, Feb. 1993, pp. 187–193.

James H. Morrissey, "Silver Stain for Proteins i Polyacrylamide Gels: A Modified Procedure with Enhanced Uniform Sensitivity," Analytical Biochemistry 117, 1981, pp. 307–310.

Poole et al, "Sequence and Expression of the Discoidin I Gene Family in *Dictyostelium Discoideum*," J. Mol. Biol., 153, 1981, pp. 273–289.

Stephen J. Poole and Richard A. Firtel, "Conserved Structural Features are Found Upstream from the Three Co–Ordinately Regulated Discoidin I Genes of *Dictyostelium Discoideum*," J. Mol. Biol., 172, 1984, pp. 203–220.

Reymond et al., "Anchoring of an Immunogenic *Plasmodium Falciparum* Circumsporozoite Protein on the Surface of *Dictyostelium Discoideum*," The Journal of Biological Chemistry, vol. 270, No. 21, Issue of May 26, 1985, pp. 12941–12947.

Roggero et al., "Synthesis and Immunological Characterization of 104–MER and 102–MER Peptides Corresponding to the N–and C–Terminal Regions of the *Plasmodium Falciparum* CS Protein," Molecular Immunology, vol. 32, No. 17/18, 1995, pp. 1301–1309.

Romanos et al., "Production of a Phosphorylated GST::HPV–6 E7 Fusion Protein Using a Yeast Expression Vector and Glutathione S–Transferase Fusions," Gene, 152, 1995, pp. 137–138.

Rowekamp et al., "Analysis of the Multigene Family Coding the Developmentally Regulated Carbohydrate–Binding Protein Discoidin–I in D Discoideum," Cell, vol. 20, Jun. 1980, pp. 495–505.

Simpson et al., "Discodin, a Developmentally Regulated Carbohydrate–Binding Protein from *Dictyostelium Discoideum*. Purification and Characterization," Biochemistry, vol. 13, No. 17, 1974, pp. 34873493.

Donald B. Smith and Kevin S. Johnson, "Single–Step Purification of Polypeptides Expressed in *Escherichia Coli* as Fusions with Glutathione S–Transferase," Gene, 67, 1988, pp. 31–40.

Springer et al., "Discoidin I Is Implicated in Cell–Substratum Attachment and Ordered Cell Migration of Dictyostelium Discoideum and Resembles Fibronector," Cell, vol. 39, Dec. 1984 (Part 2), pp. 557–564.

Maurice Sussman, "Cultivation and Synchronous Morphogenesis of Dictyostelium Under Controlled Experimental Conditions," Methods in Cell Biology, vol. 28, 1987, pp. 8–29.

Tsang et al., "The Multiple Subunits of Discoidin I Are Encoded by Different Gene," Developmental Biology 84, 1981, pp. 212–217.

Witke et al., "Homologous Recombination in the Dictyostelium $_\alpha$–actinin Gene Leads to an Altered mRNA and Lack of the Protein," The EMBO Journal, vol. 6, No. 13, 1987, pp. 4143–4148.

Early et al., "Structural Characterization of *Dictyostelium Discoideum* Prespore–Specific Gene D19 and of Its Product, Cell Surface Glycoprotein PsA," Molecular and Cellular Biology, Aug. 1988, pp. 3458–3466.

* cited by examiner

EXPRESSION VECTOR FOR USE IN A ONE-STEP PURIFICATION PROTOCOL

The present invention relates to a novel expression vector that can be used with a novel purification protocol in the production of polypeptides.

Increasing the level of expression of a recombinant protein in a particular host and simplifying the downstream processing steps are essential to produce relevant proteins at low cost. For this purpose, new expression vectors and purification procedures have been designed based, among other principles, on the presence of specific peptidic tags for affinity purification (Smith and Pidgeon U.S. Pat. No. 4,569,794; Sharma U.S. Pat. No. 5,594,115; Romanos et al., 1995; Kim and Raines, 1993; Kroll et al., 1993; Smith and Johnson, 1988), detection and/or stabilisation of the recombinant protein (Riggs, U.S. Pat. No. 4,366,246; LaVallie et al., 1993). These tags can often be removed by proteolytic or chemical cleavage (Hopp et al U.S. Pat. No. 4,782,137; Beghdadi et al., 1998) thus allowing the production of a recombinant polypeptide devoid of any extraneous amino acids.

The major disadvantage of known methods based on a peptidic tag is the use of special resins for affinity purification, which complicates large scale purification and lead to high production costs. Furthermore, metal ion based technologies result in the modification of some residues of the proteins, whereas in other cases elution solvents and procedures interfere with the catalytic activity of the purified proteins.

It is therefore the object of the present invention to provide a new expression system that enables easy and efficient purification of the polypeptide produced low cost resins. More in particular, it is the object of the invention to provide an expression system that enables purification on Sepharose 4B, a low cost resin already used in large scale purification procedures.

This is achieved according to the invention by an expression construct for the production of recombinant polypeptides, which construct comprises an expression cassette at least consisting of the following elements that are operably linked:

a) a promoter;
b) the coding region of a DNA encoding a lectin binding protein, in particular of a DNA encoding a member of the discoidin protein family, as a purification tag sequence;
c) a cloning site for receiving the coding region for the recombinant polypeptide to be produced; and
d) a transcription termination signal.

For practical use the construct is preferably contained in an expression vector, such as a plasmid suited for the transformation of a desired host.

In the research that led to the present invention the possibility of using Discoidin I, a developmentally regulated lectin in *D. discoideum*, as a tag for the production and purification of recombinant proteins was explored by means of *Dictyostelium discoideum* expression vectors (which are for example described in Fasel and Reymond U.S. Pat. No. 5,736,358). Furthermore, addition of a signal peptide can be used to re-route the expressed protein to the endoplasmic reticulum, allowing secondary modifications and secretion (Reymond et al., 1995).

The discoidins are encoded by a developmentally regulated multigene family (Poole and Firtel, 1984; Rowekamp et al., 1980; Tsang et al., 1981). Two discoidin classes, I and II, have been described in *D. discoideum*. Both are tetrameric proteins which can be distinguished by subunit molecular weight (2528 kDa range), isoelectric point, and peptide map (Frazier et al., 1975). One single gene encoding Discoidin II has been identified in *D. discoideum* while Discoidin I has been implicated in cell-substratum adhesion and ordered cell migration during aggregation. This activity seems to depend however on the fibronectin-like cell binding site of discoidin I, which is distinct from its carbohydrate binding site (Springer et al., 1984). Although most of discoidin accumulates within the cell, a certain amount is secreted by an as yet unknown pathway, probably included in multillamelar bodies (Barondes et al., 1985). Discoidins do not contain any ER translocation signals and therefore, these proteins are neither externalised via the usual secretory pathway, nor glycosylated, although several potential N-glycosylation sites are present in their sequence.

It has now been found according to the invention that the lectin-like, galactosyl-binding activity of discoidins can be exploited for purifying fusion proteins containing a discoidin and a polypeptide to be expressed, by affinity chromatography on Sepharose-4B and N-acetylgalactosamine-conjugated agarose thus leading to an integrated system for the expression and purification of recombinant proteins.

Particular advantages of the invention are that elution is obtained with galactose, a solvent which does not interact with and/or modifies the majority of the proteins. A further advantage is that discoidin in itself is non toxic and can be readily detected with specific antibodies. Even more, the production level of the desired protein can increase when expressed as a fusion with discoidin. Finally, no protein from *E. coli*, mammalian cells, or Dictyostelium, except discoidins, seems to bind specifically to Sepharose and to be released by galactose, thus reducing the level of contaminants in the purified samples.

In the expression vector of the invention the purification tag sequence is for example located upstream of the cloning site and downstream of the promoter. An alternative is to place the purification tag after the desired protein cloning site. In both cases the fusion of the purification tag with the desired protein will allow purification on the specified resins.

In order to enable easy separation of the tag from the polypeptide to be expressed, a cleavage site is preferably located in between the purification tag and the desired protein cloning site. The cleavage site is for example a thrombin cleavage site. Other possible cleavage sites are Factor X, or chemical cleavage, especially with CNBr. The thrombin cleavage site consists of a DNA sequence encoding the amino acid sequence LVPRGSDP.

The discoidin itself is not automatically routed to a specific cell compartment because it does not encompass signal sequences. Therefore, in some embodiments, the expression vector can further contain a sequence encoding a signal peptide for targeting the polypeptide to be produced to a specific cell compartment. This signal sequence is usually located downstream of the promoter and upstream of the fusion of the purification tag and the desired protein sequence. Advantageously the signal peptide for targeting is for routing the polypeptide to the endoplasmatic reticulum, such as a 21 amino acid leader peptide from the prespore antigen (PsA) protein. This is advantageous because the polypeptide to be produced can then be glycosylated and secreted.

In a first embodiment of the invention the discoidin that constitutes the purification tag sequence is Discoidin I. Another suitable discoidin is Discoidin II, or any other lectin binding protein able to bind galactose polymers.

The invention according to a further aspect thereof relates to a method for producing a polypeptide, comprising:

a) preparing an expression vector for the polypeptide to be produced by cloning the coding sequence for the polypeptide into the cloning site of an expression vector of the invention;

b) transforming a suitable host cell with the expression vector thus obtained;

c) culturing the host cell under conditions allowing expression of a fusion polypeptide consisting of the amino acid sequence of the purification tag with the amino acid sequence of the polypeptide to be expressed covalently linked thereto;

d) isolating the fusion polypeptide from the host cell or the culture medium by means of binding the fusion polypeptide present therein through the amino acid sequence of the purification tag to a polysaccharide matrix and eluting the fusion polypeptide from the matrix; and e) removing the amino acid sequence of the purification tag.

In case the vector contains a clevage site, the removal of the purification tag is performed by cleaving the amino acid sequence of purification tag of the fusion polypeptide through the cleavage site.

In the case of Discoidin I, the polysaccharide matrix is preferably Sepharose 4B in the form of beads material because, this material is cheap and purifies mainly Discoidin I and II. The elution can then be performed with galactose. An agarose matrix having N-acetylgalactosamine groups conjugated thereto is a particularly suitable matrix as a second step, because of the relatively greater affinity of Discoidin I over Discoidin II for this matrix.

The invention further relates to the novel fusion polypeptide obtainable by means of the method and to the use of these fusion polypeptides in the production of recombinant polypeptides.

The word "promoter" as used in this application is intended to encompass a cis-acting DNA sequence located 5' upstream of the initiation site of the coding sequence for a polypeptide to which DNA sequence an RNA polymerase may bind and initiate correct transcription, and optionally also encompasses enhancers.

A "fusion protein" is the combination of the amino acid sequence of the discoidin and the amino acid sequence of the polypeptide to be expressed.

The term "discoidin" is intended to relate to a lectin binding protein with affinity for galactose polymers.

All other terms used have the meaning that is generally accepted in the art and for example as given in "Dictionary of Gene Technology" by Günter Kahl, VCH, Weinheim, Germany (1995).

The following abbreviations are used in this specification:

ER: Endoplasmic reticulum
CS: Plasmodium Circumsporozoite protein
DisPf150, Dis-PfCter, Dis-PyCter: Fusion proteins comprising a Discoidin Ia amino-terminal tag and, respectively, residues $Leu_{19}$ to $Cys_{382}$ or $Lys_{282}$ to $Cys_{382}$ of $P.$ $falciparum$ CS or residues $Asn_{277}$ to $Ser_{345}$ of $P.$ $yoelii$ CS. SP-Dis-PyCter, Dis-PyCter carrying an amino terminal
ER-translocation signal
TCA: Trichloroacetic acid
PBS: Phosphate buffer saline
mAB: monoclonal antibody The invention is further illustrated in the following example, in which the expression and purification of various forms of the circumsporozoite protein (CSP) both from *Plasmodium falciparum* (Pf) and *Plasmodium yoelii* (Py) as Discoidin I fusion proteins is described as a model system. It is clear that the system is suitable for all other polypeptides that are expressed recombinantly. These examples are not meant to be restrictive, and discoidin fusion proteins can be expressed in other hosts, like *E. coli*, yeast, bacculo virus, or mammals. Furthermore, the galactose binding moiety of the discoidin, or the entire discoidin, may be synthesized chemically and added to a desired polypeptide.

In the example reference is made to the following figures:

FIG. 1

Map of the Dis-tagged Fusion Proteins

The *D. discoideum* transformation vector pEDII CS150 was modified by replacing the Discoidin promoter by an Actin 6 promoter. The entire Discoidin I coding region was amplified by PCR with concomitant addition of a downstream sequence encoding a Thrombin cleavage consensus site. The PCR product was inserted in frame with the CS coding region. Dis-PyCter and Dis-PfCter were obtained by replacing the BamHI/SacI Pf150 fragment with PCR amplification products obtained from CSP genes of *P. yoelii* and *P. falciparum* respectively as described in Materials and Methods. SP-Dis-PyCter was derived from DisPyCter by replacing the actin 6 promoter by a PCR product containing an actin 15 promoter followed by the *D. discoideum* PsA signal peptide coding sequence. (74–229)Dis-Pf150 was engineered by replacing the discoidin coding sequence by a PCR product encoding residues 74 to 229.

FIG. 2

Expression and Affinity Purification of Dis-PfCter

Soluble extracts from $~4\times10^8$ Dis-PfCter-expressing cells were chromatographed on a 1 ml Sepharose-4B column as described in Materials and Methods. Bound protein was eluted with 0.3 M galactose in TBS and 0.7 ml fractions were collected.

A. Western blot analysis using mouse polyclonal antibody raised against the PfCter carboxy-terminus. Specificity of the antibody was verified by analysing the soluble fraction from DP4 control cells (lane 1). Lanes 2–7 show Dis-PfCter purification fractions: lane 2 shows soluble extracts; lane 3 shows non-retained fraction; lanes 4–7 show fractions 1–4 eluted with 0.3 M galactose.

B and C. Coomassie-Blue/Bismarck Brown staining of gels with Dis-PfCter and DP4 fractions, respectively. Lane 1 shows the soluble fraction; lane 2 shows the flow-through lanes 3–6 show fractions 1–4 eluted with 0.3 M galactose.

Arrow indicates position of the recombinant protein of about 44 kDa. Around 15 μg protein were loaded for each of the total and flow-through samples. For galactose-eluted fractions, a sample volume corresponding to 1/50 of the fraction volume was charged in each lane.

FIG. 3

Expression and Affinity Purification of Dis-PyCter

Figure 2:
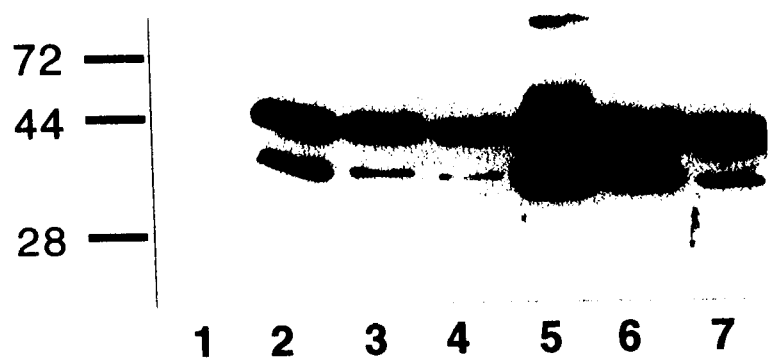
Figure 2:
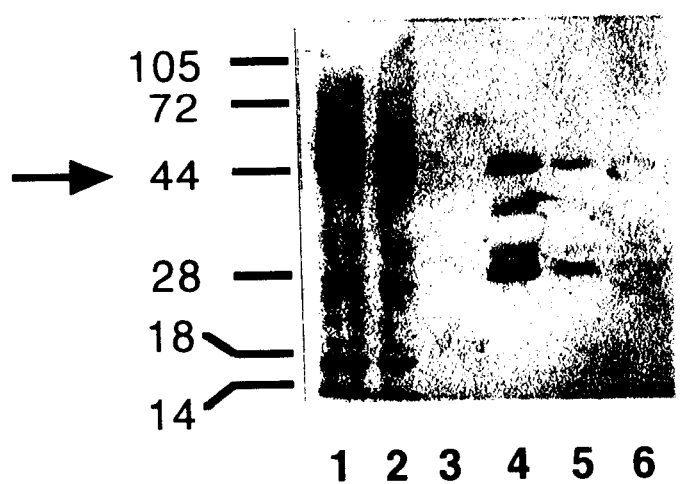
Figure 2:
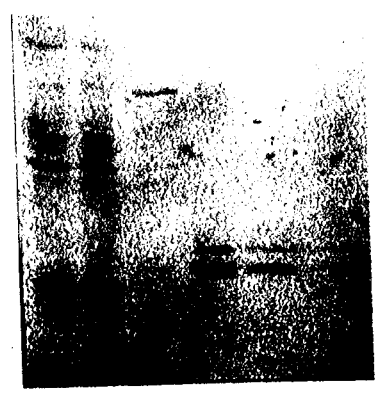

A. Western blot analysis of Dis-PyCter fractions using the J-III mouse polyclonal antibody (see Materials and Methods). Soluble cell extracts were purified as described in FIG. 2. Lane 1 shows the soluble fraction; lane 2 shows the flow-through fraction; lanes 3–4 show fractions 2–3 eluted with 0.3 M galactose; lane 5 shows how specificity of the antibody was verified by running in parallel soluble extracts from DP4 control cells.

B. and C. Coomassie blue staining of 12% gels containing Dis-PyCter (B) and DP4 (C) Sepharose-purification fractions. Lane 1 shows the soluble fraction; lanes 2–4 show galactose elution fractions 2–4.

Arrow indicates position of the recombinant protein of about 35 kDa.

FIG. 4

Expression and Affinity Purification of Dis-Pf150

A. Soluble cell extracts were purified as described in FIG. 2 by Sepharose-chromatography. After running samples in a 10% gel, Dis-Pf150 was detected in Western blots using SP3E9 mouse (see Materials and Methods). Lane 1 shows the soluble fraction; lane 2 shows non-retained protein; lanes 3–4 show 0.3 M galactose elution fractions 2 and 3, respectively; lane 5 shows how the specificity of the antibody was verified by analysing in parallel DP4 extracts.

B. Dis-Pf150 and (74–229)Dis-Pf150 cells were grown in HL5 up to a density of about $5 \times 10^6$ cells/ml. After centrifugation at about 500 g, equivalent aliquots of both cell pellet (C) and medium supernatant (M) were separated by SDS-PAGE electrophoresis and CSP was detected by Western blottindg as in A.

C. (74–229)Dis-Pf150 soluble cell extracts were handled as described in FIG. 2 and analysed by Western blot as in section A. Lane 1 shows the soluble fraction; lane 2 shows non-retained protein; lanes 3–6 show 0.3 M galactose elution fractions 1–4.

Arrow indicates position of the recombinant protein of about 84 kDa. Around 15 µg protein were loaded for each of the total and flow-through samples.

FIG. 5

Glycosylation of SP-Dis-PyCter

SP-Dis-PyCter (lanes a and b) and Dis-PyCter (lanes c and d) lysates were treated with either reaction buffer (K) or PN-Glycanase F (G) (lanes 2 and 4) (lanes 1 and 3) according to the manufacturer's instructions. After 1 h incubation at 37° C., the reaction was stopped by addition of 4×Laemmli sample buffer and PyCter was analysed by SDS-PAGE electrophoresis on a 12.5% gel and Western blotting using J-111 mouse serum.

FIG. 6

Thrombin Cleavage of Dis-PyCter

SP-Dis-PyCter expressing cells were lysed as described in Materials and Methods with the exception that protease inhibitors were omitted from the lysis buffer. Extracts were incubated at 25° C. in the presence of increasing concentrations of thrombin as indicated (units/ml). PyCter was than detected as described in FIG. 5.

EXAMPLE

Introduction

This example describes the construction of a new expression vector which allows production of fusion proteins in *Dictyostelium discoideum*. Use is made of the ability of Discoidin I to bind Sepharose-4B to set up a nearly single step purification procedure. The Discoidin I coding region is fused to several forms of the malaria parasite CSP gene in a Dictyostelium expression vector, allowing intracellular accumulation as well as partial secretion via a pathway unrelated to the endoplasmic reticulum and Golgi. The fusion proteins present in cell extracts were affinity-purified over Sepharose-4B columns. Addition of a signal peptide allows endoplasmic reticulum targeting and glycosylation of the fusion protein. Inclusion of a thrombin cleavage site allows to cleave Discoidin from the CSP protein. The use of stable and low cost Sepharose 4B as affinity matrix should allow large-scale preparations.

Materials and Methods

1. Reagents

Nitrocellulose membranes were from Schleicher & Schuell (Dassel, Germany). ECL-western blot reagents were purchased from Amersham.

Sepharose 4B was from Pharmacia (Uppsala, Sweden). D(+)galactose, peroxidase-conjugated Protein A, tunicamycin, and human thrombin were purchased from Sigma (St. Louis, Mo.). Peptide: N-glycosidase F (PNGase F) was from New England Biolabs (Beverly, Mass.) and protease inhibitors from Boehringer (Mannheim, Germany).

Peroxidase-coupled goat anti-mouse immunoglobulins were from Nordic Immunological Laboratories (Tilburg, The Netherlands). Immunoglobulins against the $(NANP)_3$ repeat were purified from the SP3E9 hybridoma cell (Boulanger et al., 1988).

Mouse serum IV-4 was raised against a synthetic peptide comprising amino acids 282–382 from the carboxy-terminal region of *P. falciparum* CSP (Roggero et al., 1995). Mouse serum J-III was raised against a synthetic peptide comprising amino acids 277–344 from the carboxy-terminal region of *P. yoelii* CSP (M. A. Roggero and G. P. Corradin, unpublished results).

2. DNA Constructs

The Dis-Pf150 construct derives from pEDII-C150 (Reymond et al., 1995) in which the Discoidin promoter is replaced by the actin 6 promoter and the CsA signal peptide by the Discoidin Ia coding region. The actin 6 promoter was amplified by PCR from the pDNeoII plasmid (Witke et al., 1987) using the oligonucleotide 5' GCGCTCGAGACTA-GAGAGGTTTATTTTTAA3' (SEQ ID NO:1), as 5' amplimer, which hybridizes to 20 nucleotides of the actin 6 promoter and contains the XhoI restriction site upstream of this sequence. As 3' amplimer, the oligonucleotide 5' TTCTCTAGACATTTTATATTATATTTATTTATTTG3' (SEQ ID NO:2) was used. This hybridizes to 23 nucleotides of the actin 6 promoter and contains an ATG initiation codon and the XbaI restriction site.

The amplified fragment starts at nucleotide 1663 and ends with initiation codon ATG (nucleotide 948). After an XhoI/XbaI double digestion, the DNA fragment was inserted into the vector pEDII-CS 150 from which the XhoI/XbaI insert containing the discoidin promoter had been eliminated.

The Discoidin Ia coding region was amplified using a BamHI linearized pWR7 plasmid (Poole et al., 1981) as template and 5' ATGTCTAGACAAGGTTTAGT-TCAACTCCTCG3' (SEQ ID NO:3) and 5' ATGAA-TTCTGGATCCGAACCACGTGGAACTAATTCCAAAG-CGGTAGCAATGT3' (SEQ ID NO:4) as 5' and 3' amplimers respectively.

The 5' amplimer corresponds to the first 33 bases from the discoidin coding region and provides a XbaI restriction site. The 3' amplimer starts with 33 bases starting with a EcoRI restriction site and a thrombin cleavage site encoding sequence, optimized for *D. discoideum* codon usage, followed by a stretch which hybridizes with the last 20 bases of the discoidin encoding region. The fusion gene encodes a 629 amino acid long polypeptide comprising the discoidin tag ($Met_1$ to $Met_{257}$) and a 364 amino acid-long *P. falciparum* CSP fragment ($Leu_{19}$ to $Cys_{382}$) between which an 8 amino acid-long thrombin recognition site (LVPRGSAP) has been introduced.

To obtain expression of a 101 amino acids C-terminal segment of *P. falciparum* CSP ($Lys_{282}$ to $Cys_{382}$) the corresponding DNA was amplified from the CS NF54 gene (Caspers et al., 1989) using 5' GGTGGATCCAGGAAT-TCAAAAAAACAATCAAGGTAATGGA3' (SEQ ID NO:5) and 5' AAGCGAGCTCTTAACATMCCAT-MACAAAT3' (SEQ ID NO:6) as 5' and 3' amplimers respectively.

The 5' amplimer hybridized to 21 nucleotides of the CSP gene. Upstream of the CSP sequence, the 5' amplimer contained the BamHI restriction site and 10 nucleotides representing an EcoRI restriction site and coding for amino acids G, I and Q.

The 3' amplimer hybridized to 22 nucleotides of the CSP gene and enabled the insertion of an in-frame UAA and of the SacI restriction site into the gene. After a BamHI/SacI double digestion, the resultant fragment was used to replace the corresponding insert in the DisPf150 expression vector. The resulting gene codes for a 369 amino acid-long polypeptide comprising 257 residues of the Discoidin tag, the 8 residues of the thrombin cleavage site and 108 amino acids from the CS gene.

The Dis-PyCter construct was engineered similarly to Dis-PfCter, with the exception that a PCR product encoding the C-terminal segment ($Asn_{277}$ to $Ser_{345}$) from the CS gene was amplified from *P. yoelii* 17X (de la Cruz et al., 1988) DNA and used to replace the BamHI/SacI insert in the Dis-Pf150 expression vector. The following 35 two oligonucleotides were used as 5' and 3' amplimers, respectively:

5' GGTGGATCCAGGAATTCAAAATGAAGAT-TCTTATGTCCCA3' (SEQ ID NO:7)

5' CGTACGAGCTCTTAAGATATCAATGAA-CAMATCCATMAC3' (SEQ ID NO:8)

The 5' amplimer hybridized to 21 nucleotides of the CSP gene. Upstream of the CSP sequence, the 5' amplimer contained the BamHI restriction site and 10 nucleotides representing an EcoRI restriction site and coding for amino acids G, I and Q.

The 3' amplimer hybridized to 20 nucleotides of the CSP gene and enabled the insertion in the gene of 12 additional nucleotides containing an EcoRV restriction site and encoding a Lys-Ile-Ser linker between amino acids L, I, S and an in-frame UAA stop codon upstream of the SacI restriction site. The resulting gene encodes a 340 amino acids-long polypeptide including the 257+8 discoidin-thrombin-site sequence followed by 79 residues of *P. yoelii* CSP.

The expression vector for a Dis-PyCter fusion protein containing an amino-terminal ER-translocation signal peptide (PS-Dis-PyCter) was derived from the Dis-PyCter expression vector (described above) in which the actin 6 promoter has been replaced by an actin 15 promoter (Knecht et al., 1986) followed by the sequence of the *D. discoideum* PsA signal peptide (Early et al., 1988). The *D. discoideum* PsA leader peptide (amino acids 1–21) was amplified by PCR from the pMUW1630 vector (K. Williams and M. Slade, School of Bioogical Scences, Macquarie University, Sydney, Australia), using 5' AGCTCGAGATTCACAAAT-TAATTAATCCCATC3' (SEQ ID NO:9) and 5' AATCTA-GATTCATATGCATTGGCGTATGTTAA3' (SEQ ID NO:10) as 5' and 3' amplimers.

The 5' amplimer hybridized to 20 nucleotides of the actin 15 promoter and contains the XhoI restriction site upstream of this sequence. The 3' amplimer hybridized to 24 nucleotides of the PsA gene and contains an XbaI restriction site downstream of this sequence. After amplification and digestion with restriction enzymes XhoI and XbaI, the DNA fragment was inserted into the Dis-PyCter vector to replace the actin 6 promoter.

The final vector encodes a protein starting with the first 21 amino acids of the PsA protein (cleavage of the leader peptide takes place after residue 19) fused to the second amino acid of Discoidin Ia (amino acids position 3 T→R). Thus, cleavage of the signal peptide during processing of the protein leads to a fusion protein which is only 1 amino acid longer than the one obtained by expression of the Dis-PyCter construct.

A truncated form of Dis-Pf150, (74–229)Dis-Pf150), was constructed by amplifying the DNA region encoding discoidin Ia residues $Val_{74}$ to $Asp_{229}$ in Dis-Pf150 by PCR using the following oligonucleotides (3' and 5' amplimers respectively):

5' AATCTAGAGTTGCTGCTCTCCAAGGTCGTGGT3' (SEQ ID NO: 11)

5' AGGGATCCATATCGAAACCMGGTGG-TAATGTT3' (SEQ ID NO: 12).

The PCR product was inserted next to the actin 6 promoter in a way similar to the construction of Dis-Pf150, whereas the signal peptide was replaced by the truncated Discoidin I.

3. Cell Culture and Transfection

*D. discoideum* cells of the axenic strain AX2 were transfected by electroporation with plasmids as described in Anjard et al. (1992). Clonal transformants were selected by growing under G418 selection on *Micrococcus luteus* PRF3 lawns (Wilczynska and Fisher, 1994). Stable cell lines were selected by growing cells at 22° C. in HL5 medium (Sussman, 1987) in the presence of increasing G418 concentrations up to 50–100 µg/ml.

4. Purification of Recombinant Proteins

Cultures were grown in HL5 up to a density of ca. $7 \times 10^6$ cells/ml. Cells were harvested by 5 min. centrifugation at 300 g after which pellets were resuspended at a ratio of $2 \times 10^8$ cells/ml in lysis solution containing 1% Triton X-100, 5 mM benzamidine, 0.1 units/ml aprotinin, 50 µg/ml trypsin inhibitor and 2 µg/ml antipain in TBS (25 MM Tris, pH 7.4, 137 mM NaCl, 2.7 mM KCl). After 1 cycle of freezing and thawing, lysates were centrifuged for 15 min. at 10,000 g at 5° C. $CaCl_2$ was adjusted to 10 mM in supernatants which were then loaded onto Sepharose-4B columns preequilibrated in lysis solution supplemented wit 10 MM $CaCl_2$. 1 ml bed volume was used per $4 \times 10^8$ cells. Columns were washed with 20 bed volumes of TBS, 10 mM $CaCl_2$ containing protease inhibitors. Protein was eluted with 0.3 M galactose in TBS, 0.7 bed volumes per fraction. ca. 90% of the fusion protein eluted in fractions 2–4.

5. Gel Electrophoresis and Immunoblotting

15 µl samples of purification fractions or 2 _1 from the soluble fraction of the initial lysates (Total fraction) were prepared with 3×Laemmli sample buffer (Laemmli, 1970) containing 200 mM DTT, heated for 10 min. at 80° C. For Sepharose flow-through fractions, the volume loaded was adjusted as to have the same amount of protein as in the Total fraction. Protein was revealed by either Coomassie-Blue/Bismarck Brown R staining (Choi et al., 1996) or silver stain (Morrissey, 1981). Western blots were performed by semi-dry electrotransfer onto nitrocellulose. After blocking in PBS containing 4% skimmed milk, membranes were incubated in the presence of different types of sera or mAbs, such as the Sp3E9 mAb which was raised against a synthetic $(NANP)^{50}$-repeat, as shown in the figures.

After 3 washes in PBS, 0.02% Tween, the membrane was incubated for 1 h in the presence of either peroxidase-coupled goat anti-mouse serum diluted 1/2,000 in PBS-milk or peroxidase-conjugated Protein A. After washing the membrane, immunostaining was revealed using an ECL kit according to the manufacturer's instructions.

RESULTS

1. Expression and Purification of Intracellular Discoidin-tagged Proteins

The potential of Discoidin I to be used as a tag for protein purification was evaluated by fusing it to a fragment of carboxy-terminus of the CSP protein of *P. falciparum* (PfCter) comprising amino acids 282–382 (FIG. 1). The Discoidin I coding region was amplified by PCR from genomic DNA and convenient restriction sites were added, in order to generate a fragment compatible with a *D. discoideum* expression vector (cf. Materials and Methods). The resulting vector, pAC6-Dis-PfCter, was used to transform axenic Ax2 *D. discoideum* cells by electroporation.

After selection of stable transformants with G418 at concentrations up to 50 μg/ml, expression of the fusion protein was analysed by immunoblotting and compared to cells transfected with a vector carrying only the selectable marker (DP4) (Anjard et al., 1992).

A mouse serum (IV-4) raised against the C-terminal peptide of *P. falciparum* (Roggero et al., 1995) detected a protein of 44 kDa on Western blots, the size expected for the Dis-PfCter protein, which was absent from the control DP4 strain (FIG. 2A). The presence of a lower band indicates that either partial degradation or incomplete synthesis of the protein may take place. Accumulation of Dis-PfCter varied with cell density and was maximal around ~7×10$^6$ cells/ml.

A purification protocol for Discoidins I and II using Sepharose 4B chromatography (Simpson et al., 1974) allowed partial purification of Dis-PfCter (FIGS. 2A and C). A 44 kDa protein (arrow) eluted from the resin in the second and third fractions upon 0.3 M galactose addition, together with endogenous discoidins (25 and 28 kDa). An intermediary band of about 35 kDa was also observed, as on Western blots. The absence of both 44 and 35 kDa proteins in DP4 fractions (FIG. 2B) indicated that the Coomassie blue stained bands were indeed Dis-PfCter or derivatives. Furthermore, elution using a gradient instead of 0.3M galactose showed that both Discoidin I and the recombinant protein coeluted between 200 and 220 mM galactose, whereas Discoidin II elution was slightly shifted to higher galactose concentrations (data not shown). Using such procedure, about 1–2 mg of fusion protein was isolated per liter of culture, as determined by Bradford assays (Bradford, 1976) and densitometric analysis of Coomassie-stained gels (Choi et al., 1996). The calculated purification factor is about a 30-fold. The recovery efficiency varied between 50 and 70% as determined by western blot analysis, depending mainly on the Sepharose/protein ratio used in the experiment. Taking these results together, it can be estimated that the Dis-PfCter represents at least 1% of the *D. discoideum* soluble proteins.

Figure 3:
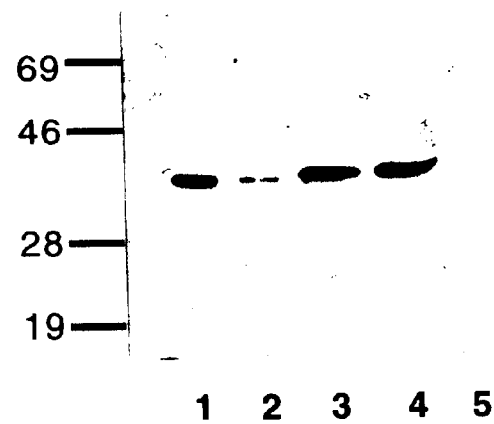
Figure 3:
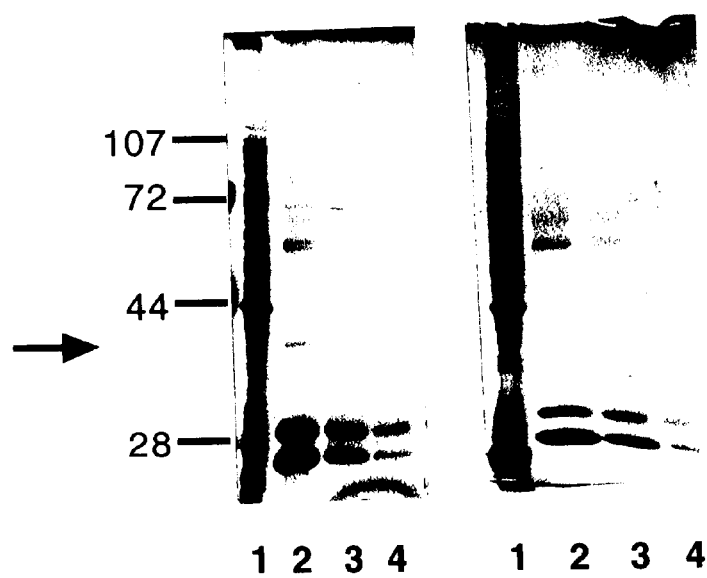

It was further analysed whether other proteins could be linked to the Dis-tag without interfering with its Sepharose binding ability. The C-terminal region of the CSP from *P. yoelii* (PyCter) has a different amino acid composition than PfCter (de la Cruz et al., 1988). The DNA encoding residues 277–344 of *P. yoelii* CSP was cloned in frame with the Discoidin I coding sequence and the resulting gene placed under the control of an actin 6 promoter. A mouse serum (J-111) raised against the carboxy terminus of *P. yoelii* CSP (see Materials and Methods) detected a band of about 35 kDa in *D. discoideum* cells transformed with the pAC6-Dis-PyCter plasmid (FIG. 3A). Binding of the Dis-PyCter fusion protein to Sepharose-4B and elution with galactose resembled that of Dis-PfCter (FIG. 3A), allowing the detection of a protein of about 35 kDa by Coomassie blue staining. The Dis-PfCter protein accumulated to about 0.2 mg per liter of culture. These results thus confirmed the applicability of Discoidin I as a tag for the purification of recombinant polypeptides.

To check whether larger proteins could be expressed using the Discoidin I fusion vector, CS150, a form of PfFCSP lacking only the last 23 amino acids (Reymond et al., 1995), was fused to Discoidin I and expressed in *D. discoideum*. Although expressed at a lower level than Dis-PfCter, (about 0.1 mg per liter), a band of about 84 kDa was detected in immunoblots of cell lysates stained with either the SP3E9 monoclonal antibody against a (NANP)$_3$ repeat (Boulanger et al., 1988) (FIG. 4A) or mouse serum against CSP$_{282-382}$ (data not shown). This protein could be purified by Sepharose-affinity chromatography under conditions similar to those described for Dis-PfCter and Dis-PyCter.

Figure 4:
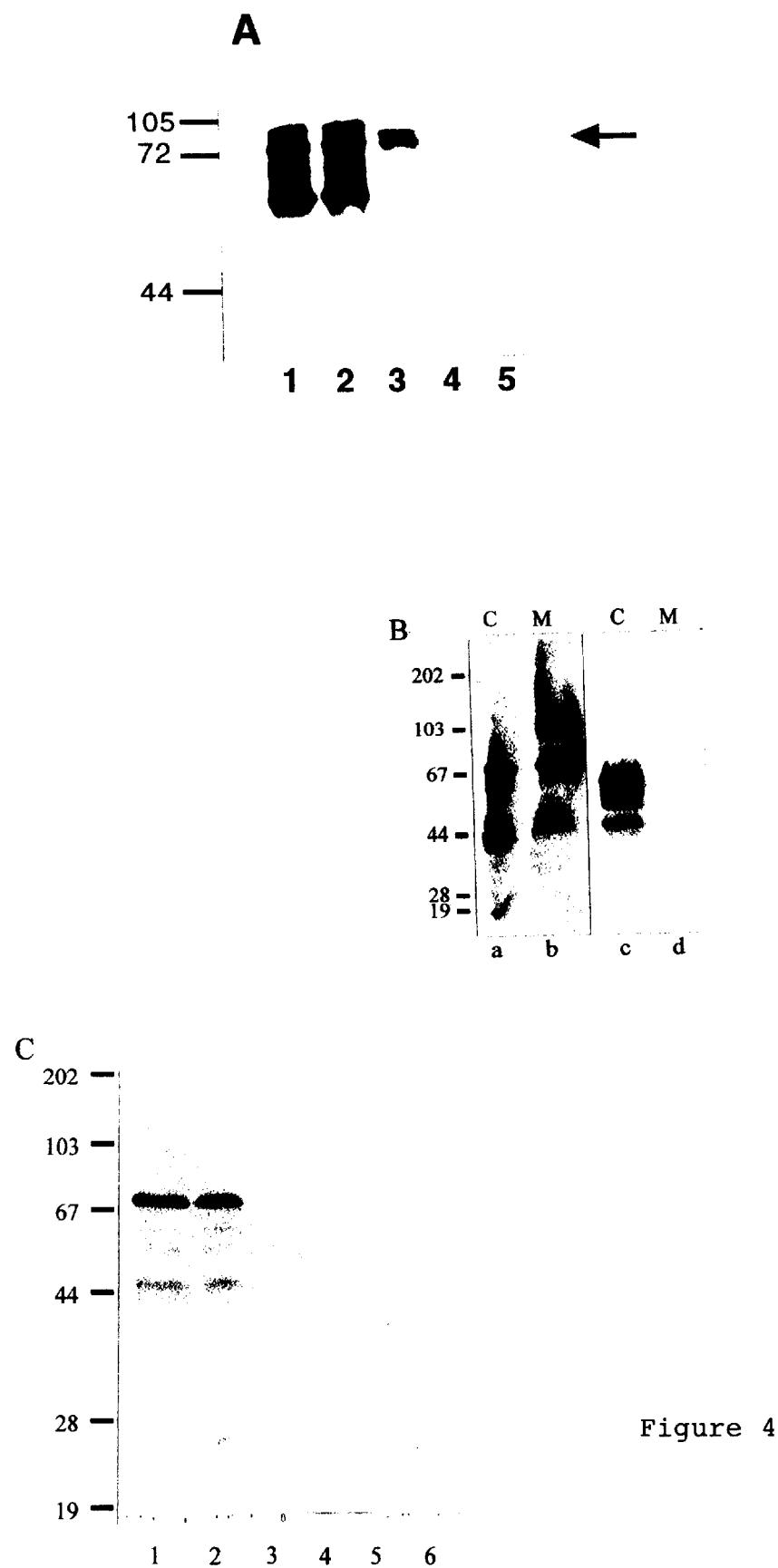

To further verify the specificity of the binding of the fusion proteins to Sepharose, the first 73 amino acids of Discoidin I were deleted and the deleted peptide fused to *P. falciparum* CS 150 ((74–229)Dis-Pf150). (74–229)Dis-Pf150 was unable to bind to Sepharose 4B indicating that residues 1 to 73 at the amino terminus of Discoidin I are essential for its binding activity (FIG. 4B).

2. Expression and Purification of Extracellular Discoidin-tagged Proteins

Since discoidins had been shown to be shed by *D. discoideum* (Barondes et al., 1983; Barondes et al., 1985), the presence of Dis-tagged proteins in the extracellular medium was investigated and their affinity to Sepharose4B evaluated. Both Dis-PfCter and Dis-Pf 150 could be detected in the culture medium by Western blots, reaching levels between 20 and 50% of the total fusion protein produced (FIG. 4C and data not shown). It was then asked whether the discoidin moiety was required for secretion by using the deletion mutant, missing the first 72 discoidin amino acids. Although (73–229)Dis-Pf150 accumulated inside the cell up to a level similar to the full-length Dis-Pf150, no fusion protein was detected in the extracellular medium (FIG. 4C). These results suggest that integrity of the discoidin tag is required for secretion to take place.

3. Addition of an ER Signal Peptide Results in N-glycosylation of Dis PyCter

The route used by Discoidins I and II to reach the extracellular space has not been thoroughly investigated. The Discoidin I amino acid sequence contains 4 potential Asn-X-Ser/Thr-X N-glycosylation sites. However, the absence of a signal peptide, as well as the lack of reports on the glycosylation of discoidins, indicate that the protein reaches the extracellular space by a pathway, which probably does not involve the endoplasmic reticulum (ER) and Golgi.

In order to specifically target the fusion protein to the ER/Golgi secretory pathway, the signal peptide from *D. discoideum* PsA cell surface antigen (Early et al., 1988) was fused to the N-terminus of Dis-PyCter. No SP-Dis-PyCter protein was secreted (data not shown). Furthermore, the SP-Dis-PyCter was unable to bind to Sepharose 4B (data not shown). The SP-Dis-PyCter protein was expressed at a similar level compared to Dis-PyCter as analysed by western blot but was about 15 kDa larger than the latter (see FIG. 5).

The difference of 15 kDa observed in cell lysates between SP-Dis-PyCter and Dis-PyCter is larger than the 19 amino acids of the signal peptide itself. Since there are 4 potential N-glycosylation sites in Discoidin I (39–42 NGTN, 97–100 NLSW, 212–215 NQTR, 222–225 NITT) plus one additional site at the expressed sequence of *P. yoelii* CSP (328–331 NLTL), the increase in size could reflect the glycosylation of the SP-Dis-PyCter.

Figure 5:
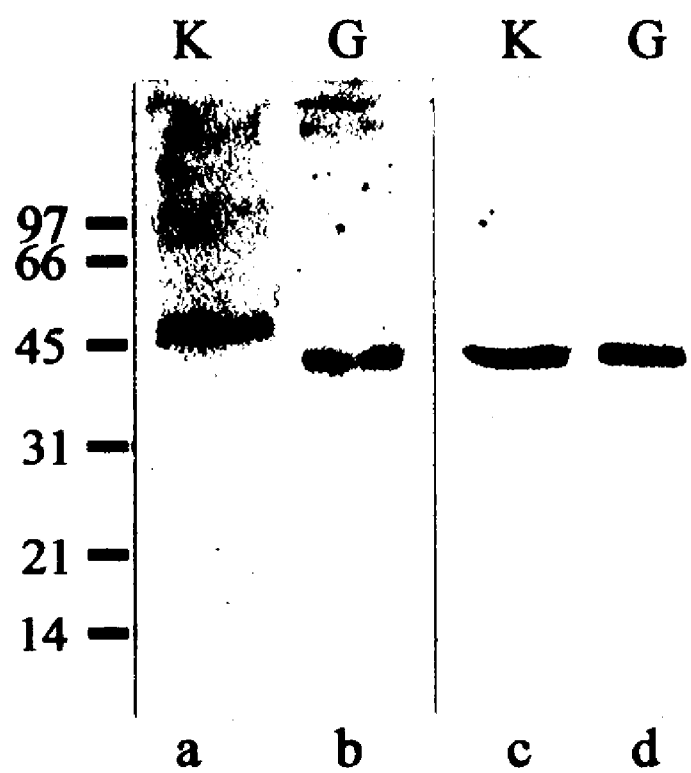

Indeed, Glycanase F treatment resulted in a size shift of the SP-Dis-PyCter band down to around 35 kDa (FIG. 5), close to that of DisPyCter. As control, treating Dis-PyCter, which lacks the PsA signal peptide, with Glycanase F did not change its migration upon SDS-PAGE electrophoresis (FIG. 5). A further confirmation of the glycosylation of SP-Dis-PyCter was obtained by adding the N-glycosylation blocker tunicamycin to the culture medium, what lead to the appearance of lower molecular weight forms (data not shown).

These results indicate that providing a signal peptide to the fusion protein results in routing of the recombinant protein to the ER/Golgi compartment where it is subsequently glycosylated.

4. Removal of the Discoidin Tag

Figure 6:
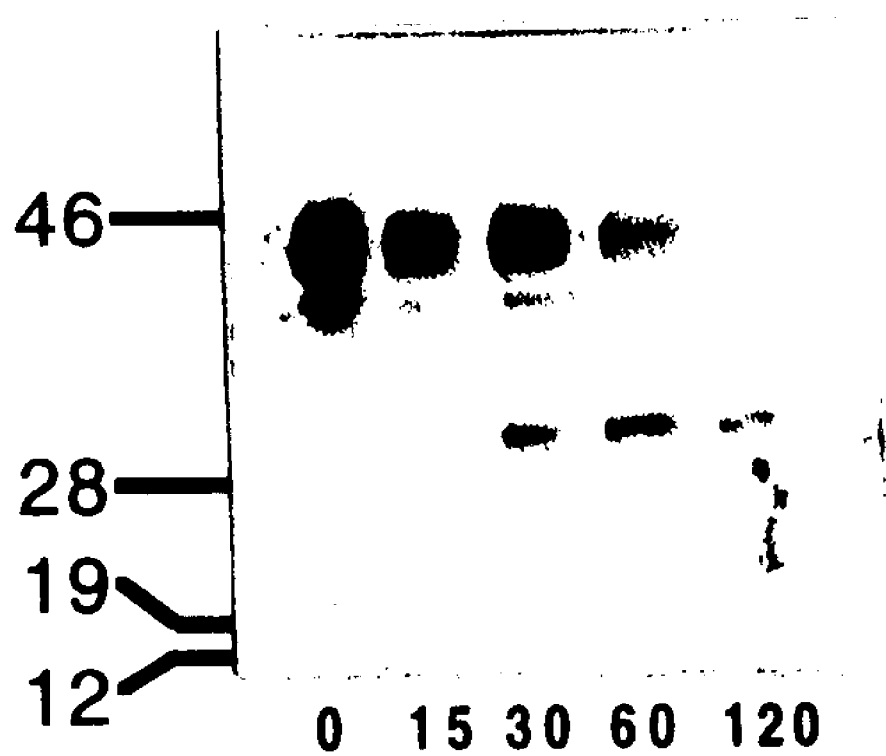

In order to allow removal of the discoidin-tag from the recombinant protein, a thrombin cleavage site was inserted between the Dis-tag and the C-terminal peptide of P. yoelii (see FIG. 1). As shown in FIG. 6, the size of the recombinant protein decreased with increasing thrombin concentrations, indicating that the discoidin-tag can be cleaved.

DISCUSSION

Fusing recombinant proteins to Discoidin I allows removal of most contaminants in a simple single step using Sepharose 4B only. Integrity of the discoidin moiety is required, since a deletion mutant was unable to bind to the affinity resin. For all cytosolic fusion proteins, the discoidin tag is fully functional in respect to Sepharose binding, with no significant difference in affinity when compared to endogenous Discoidin I. This purification system is efficient since, except for endogenous Discoidins, few other proteins are co-purified, as seen upon both Coomassie and silver staining. An additional step based on a different procedure, like ion exchange chromatography, size fractionation or HPLC, can be added to the process to separate the fusion proteins from discoidins.

In a preferred embodiment the discoidin-tag is removable from the fusion protein, allowing retention on a second passage on Sepharose 4B. For this a thrombin cleavage site is added between the Discoidin I and CSP sequences. The addition of polyglycine linkers adjacent to the protease recognition sites may further improve removal of the Discoidin I-tag.

Targeting a recombinant product towards the extracellular medium simplifies purification and allows secondary modifications. The invention further shows that routing the discoidin fusion protein to the ER and Golgi by adding the 21 amino acid leader peptide from the Prespore antigen PsA protein results in glycosylation of at least some of the P. yoelii CSP (328–331 NLTL) and Discoidin I (39–42 NGTN, 97–100 NLSW, 212–215 NQTR, 222–225 NITT) potential sites.

The invention shows that a Dicoidin tag can be used to purify fusion proteins. This property can be used in other expression systems ranging from E. coli to mammalian cells, provided that proper expression vectors are used and possibly some codons are changed in consequence. Besides, the invention further shows that D. discoideum constitutes an attractive option for the production of recombinant proteins, either as components of subunit vaccines, or for other biotechnological applications. In contrast to many types of bacteria, D. discoideum is not pathogenic and does not produce enterotoxins. For this reason, purification of proteins to be injected into animals or humans should be considerably simplified. Inunnunisation experiments have shown that cell lysates are non toxic to mice (Reymond et al., 1995) or monkeys (N. Fasel, C. Reymond, and S. Herrera, unpublished results) setting the stage for human immunisation with purified polypeptides without the risk of maintaining traces of toxic components.

Besides its simple growth requirements and the possibility of obtaining stable cell lines, D. discoideum presents various features which makes processing easier than for other organisms such as bacteria and yeast. The absence of a cell wall allows a rapid and easy lysis of the cells, by simple freezing and thawing which can be implemented by using low percentages of Triton X-100. This should simplify the isolation of delicate proteins in an active form. The introduction of a straightforward purification method based on a discoidin-tag and Sepharose-4B as a low-cost affinity matrix as proposed by this invention should improve the attractiveness of D. discoideum for biotechnology.

REFERENCES

Anjard, C., Pinaud, S., Kay, R. R., and Reymond, C. D. (1992). Overexpression of DdPK2 protein kinase causes rapid development and affects the intracellular cAMP pathway of Dictyostelium discoideum. Development 115, 785–790.

Barondes, S. H., Cooper, D. N., and Haywood-Reid, P. L. (1983). Discoidin I and discoidin II are localized differently in developing Dictyostelium discoideum. J. Cell Biol. 96, 291–296.

Barondes, S. H., Haywood, R. P., and Cooper, D. N. (1985). Discoidin I, an endogenous lectin, is externalized from Dictyostelium discoideum in multilamellar bodies. J Cell Biol 100, 1825–1833.

Boulanger, N., Matile, H., and Betschart, B. (1988). Formation of the circumsporozoite protein of Plasmodium falciparum in Anopheles stephensi. Acta Tropica 45, 55–65.

Bradford, M. M. (1976). A rapid and sensitive method for the quantitation of microgram quantities of protein utilizing the principle of protein-dye binding. Analytical Biochemistry 72, 248–54.

Caspers, P., Gentz, R., Matile, H., Pink, J. R., and Sinigaglia, F. (1989). The circumsporozoite protein gene from NF54, a Plasmodium falciparum isolate used in malaria vaccine trials. Molecular & Biochemical Parasitology 35, 185–9.

Choi, J. K., Yoon, S. H., Hong, H. Y., Choi, D. K., and Yoo, G. S. (1996). A modified Coomassie blue staining of proteins in polyacrylamide gels with Bismark brown R. Analytical Biochemistry 236, 82–4.

Cooper, D. N., Lee, S. C., and Barondes, S. H. (1983). Discoidin-binding polysaccharide from Dictyostelium discoideum. J. Biol. Chem. 258, 8745–8750.

de la Cruz, V. F., Lal, A. A., and McCutchan, T. F. (1988). Variation among circumsporozoite protein genes from rodent malarias. Molecular & Biochemical Parasitology 28, 31–8.

Early, A. E., Williains, J. G., Meyer, H. E., Por, S. B., Smith, E., Williains, K. L., and Gooley, A. A. (1988). Structural characterization of Dictyostelium discoideum prespore-specific gene D19 and of its product, cell surface glycoprotein PsA. Molecular & Cellular Biology 8, 3458–66.

Emslie, K. R., Slade, M. B., and Williams, K. L. (1995). From virus to vaccine: developments using the simple eukaryote, Dictyostelium discoideum. Trends Microbiol 3, 476–9.

Frazier, W. A., Rosen, S. D., Reitherman, R. W., and Barondes, S. H. (1975). Purification and comparison of two developmentally regulated lectins from Dictyostelium discoideum—Discoidin I and II. J. Biol. Chem. 250, 7714–7721.

Guan, K. L., and Dixon, J. E. (1991). Eukaryotic proteins expressed in Escherichia coli: an improved thrombin cleavage and purification procedure of fusion proteins with glutathione S-transferase. Analytical Biochemistry 192, 262–7.

Guan, K. L., Haun, R. S., Watson, S. J., Geahlen, R. L., and Dixon, J. E. (1990). Cloning and expression of a protein-tyrosine-phosphatase. Proceedings of the National Academy of Sciences of the United States of America 87, 15015.

Kim, J. S., and Raines, R. T. (1993). Ribonuclease S-peptide as a carrier in fusion proteins. Protein Science 2, 348–56.

Knecht, D. A., Cohen, S. M., Loornis, W. F., and Lodish, H. F. (1986). Developmental regulation of Dictyostelium discoideum actin gene fusions carried on low-copy and high-copy transformation vectors. Mol. Cell. Biol. 6, 3973–3983.

Kroll, D. J., Abdel-Malek Abdel-Hafiz, H., Marcell, T., Simpson, S., Chen, C. Y., Gutierrez-Hartmann, A., Lustbader, J. W., and Hoeffler, J. P. (1993). A multifunctional prokaryotic protein expression system: overproduction, affinity purification, and selective detection. DNA & Cell Biology 12, 441–53.

Laemmli, U. K. (1970). Cleavage of structural proteins during the assembly of the head of bacteriophage T4. Nature 227, 680–5.

LaVallie, E. R., DiBlasio, E. A., Kovacic, S., Grant, K. L., Schendel, P. F., and McCoy, J. M. (1993). A thioredoxin gene fusion expression system that circumvents inclusion body formation in the *E. coli* cytoplasm. Bio/Technology 11, 187–93.

Morrissey, J. H. (1981). Silver stain for proteins in polyacrylamide gels: a modified procedure with enhanced uniform sensitivity. Analytical Biochemistry 117, 307–10.

Poole, S., Firtel, R. A., Lamar, E., and Rowekamp, W. (1981). Sequence and expression of the discoidin I gene family in *Dictyostelium discoideum*. J. Mol. Biol. 153, 273–289.

Poole, S. J., and Firtel, R. A. (1984). Conserved structural features are found upstream from the three co-ordinately regulated discoidin I genes of *Dictyostelium discoideum*. Journal of Molecular Biology 172, 203–20.

Reymond, C. D., Beghdadi, R. C., Roggero, M., Duarte, E. A., Desponds, C., Bernard, M., Groux, D., Matile, H., Bron, C., Corradin, G., and et al. (1995). Anchoring of an immunogenic *Plasmodium falciparum* circumsporozoite protein on the surface of *Dictyostelium discoideum*. J Biol Chem 270, 12941–7.

Roggero, M. A., Filippi, B., Church, P., Hoffman, S. L., Blum-Tirouvanziam, U., Lopez, J. A., Esposito, F., Matile, H., Reymond, C. D., Fasel, N., and Corradin, G. P. (1995). Synthesis and immunological characterization of 104mer and 102-mer peptides corresponding to the N-and C-terminal regions of the *Plasmodium falciparum* CS protein. Molecular Immunology 32, 1301–9.

Romanos, M. A., Hughes, F. J., Comerford, S. A., and Scorer, C. A. (1995). Production of a phosphorylated GST::HPV-6 E7 fusion protein using a yeast expression vector and glutathione S-transferase fusions. Gene 152, 137–8.

Rowekamp, W., Pool, S., and Firtel, R. A. (1980). Analysis of the multigene family coding the developmentally regulated carbohydrate-binding protein discoidin-I in *Dictyostelium discoideum*. Cell 20, 495–505.

Simpson, D. L., Rosen, S. D., and Barondes, S. H. (1974). Discoidin, a developmentally regulated carbohydrate binding protein from *Dictyostelium discoideum*. Purification and characterization. Biochem. 13, 3487–3493.

Smith, D. B., and Johnson, R. S. (1988). Single-step purification of polypeptides expressed in *Escherichia coli* as fusions with glutathione S-transferase. Gene 67, 31–40.

Springer, W. R., Cooper, D. N., and Barondes, S. H. (1984). Discoidin I is implicated in cell-substratum attachment and ordered cell migration of *Dictyostelium discoideum* and resembles fibronectin. Cell 39, 557–64.

Sussman, M. (1987). Cultivation and synchronous morphogenesis of Dictyostelium under controlled experimental conditions. Meth. Cell Biol. 28, 929.

Tsang, A. S., Devine, M., and Williams, J. G. (1981). The multiple subunits of discoidin I are encoded by different genes. Dev. Biol. 84, 212–217.

Wilczynska, Z., and Fisher, P. R. (1994). Analysis of a complex plasmid insertion in a phototaxis-deficient transformant of *Dictyostelium discoideum* selected on a Micrococcus luteus lawn. Plasmid 32, 182–94.

Witke, W., Nellen, W., and Noegel, A. (1987). Homologous recombination in the Dictyostelium alpha-actinin gene leads to an altered mRNA and lack of the protein. EMBO J. 6, 4143–4148.

What is claimed is:

1. An expression construct for the production of recombinant polypeptides, which construct comprises an expression cassette consisting of the following elements that are operably linked:
    a) a promoter;
    b) the coding region of a DNA encoding a galactose binding protein of the discoidin family as a purification tag sequence;
    c) a cloning site for receiving the coding region for the recombinant polypeptide to be produced; and
    d) transcription termination signals, said promoter being positioned 5' to elements (b), (c) and (d), and wherein said expression construct is devoid of a signal sequence.

2. An expression construct as claimed in claim 1, wherein the purification tag sequence is placed in close proximity to the cloning site, downstream of the promoter.

3. An expression construct as claimed in claim 1, wherein a protease cleavage site is located in between the purification tag sequence and the cloning site.

4. An expression construct as claimed in claim 1, wherein the purification tag sequence encodes discoidin Ia.

5. An expression construct as claimed in claim 1, wherein the purification tag sequence encodes discoidin II.

6. An expression construct as claimed in claim 3, wherein the cleavage site is a thrombin cleavage site.

7. An expression construct as claimed in claim 6, wherein the thrombin cleavage site consists of a DNA sequence encoding the amino acid sequence LVPRGSDP (SEQ ID NO: 13).

8. An expression construct as claimed in claim 1 for use in a method for producing a polypeptide.

9. An expression vector containing an expression construct as claimed in claim 1.

10. An expression vector as claimed in claim 9 for use in a method for producing a polypeptide.

11. A method for producing a polypeptide, comprising:
    a) preparing an expression vector for the polypeptide to be produced by cloning the coding sequence for the polypeptide into the cloning site of an expression vector as claimed in claim 9;
    b) transforming a suitable host cell with the expression vector thus obtained;
    c) culturing the host cell under conditions allowing expression of a fusion polypeptide consisting of the amino acid sequence of the purification tag with the amino acid sequence of the polypeptide to be expressed covalently linked thereto; and d) isolating the fusion polypeptide from the host cell or the culture medium by means of binding the fusion polypeptide present therein through the amino acid sequence of the purification tag to a polysaccharide matrix and eluting the fusion polypeptide from the matrix.

12. A method as claimed in claim 11, wherein the purification tag is removed by cleaving the fusion polypeptide through the cleavage site.

13. The method of claim 11, wherein the matrix is Sepharose 4B and the elution is performed with galactose.

14. The method of claim 11, wherein the polysaccharide matrix is an agarose matrix having N-acetylgalactosamine groups conjugated thereto and the elution is performed with galactose.

15. The method of claim 14, wherein the Sepharose 4B matrix is in the form of beads.

16. A fusion polypeptide obtained by the method of claim 11.

* * * * *

SEQUENCE LISTING

```
<160> NUMBER OF SEQ ID NOS: 13

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: 5' amplimer

<400> SEQUENCE: 1
gcgctcgaga ctagagaggt ttatttttaa                                          30

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: 3' amplimer

<400> SEQUENCE: 2
ttctctagac attttatatt atatttattt atttg                                    35

<210> SEQ ID NO 3
<211> LENGTH: 31
<212> TYPE: DNA
<213> ORGANISM: Artificial Sequence
```

```
<220> FEATURE:
<223> OTHER INFORMATION: Description of Artificial Sequence: 5' amplimer

<400> SEQUENCE: 3
atgtctagac aaggtttagt tcaactcctc g                                    31

<210> SEQ ID NO 4
<211> LENGTH: 53
<212> TYPE: DNA
<213> ORGANISM: Artificial Sequence
<220> FEATURE:
<223> OTHER INFORMATION: Description of Artificial Sequence: 3' amplimer

<400> SEQUENCE: 4
catgaattct ggatccgaac cacgtggaac taattccaaa gcggtagcaa tgt            53

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence: 5' amplimer

<400> SEQUENCE: 5
ggtggatcca ggaattcaaa aaacaatca aggtaatgga                            40

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: 3' amplimer

<400> SEQUENCE: 6
aagcgagctc ttaacatmcc atmacaaat                                       29

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence: 5' amplimer

<400> SEQUENCE: 7
ggtggatcca ggaattcaaa atgaagattc ttatgtccca                           40

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: 3' amplimer

<400> SEQUENCE: 8
cgtacgagct cttaagatat caatgaacam atccatmac                            39

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence: 5' amplimer

<400> SEQUENCE: 9
agctcgagat tcacaaatta attaatccca tc                                   32
```

```
<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: 3' amplimer

<400> SEQUENCE: 10
aatctagatt catatgcatt ggcgtatgtt aa                                     32

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence: 3' amplimer

<400> SEQUENCE: 11
aatctagagt tgctgctctc caaggtcgtg gt                                     32

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: 5' amplimer

<400> SEQUENCE: 12
agggatccat atcgaaaccm ggtggtaatg tt                                     32

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: peptide

<400> SEQUENCE: 13

Leu Val Pro Arg Gly Ser Asp Pro
 1               5
```